United States Patent
Bishop (10) Patent No.: US 12,403,042 B2
(45) Date of Patent: Sep. 2, 2025

(54) WOUND DRESSING

(71) Applicant: ConvaTec Limited, Flintshire (GB)

(72) Inventor: Stephen Bishop, Flintshire (GB)

(73) Assignee: CONVATEC LIMITED, Flintshire (GB)

( * ) Notice: Subject to any disclaimer, the term of this patent is extended or adjusted under 35 U.S.C. 154(b) by 0 days.

(21) Appl. No.: 18/883,627

(22) Filed: Sep. 12, 2024

(65) Prior Publication Data

US 2025/0000710 A1    Jan. 2, 2025

Related U.S. Application Data

(63) Continuation of application No. PCT/GB2023/050603, filed on Mar. 15, 2023.

(30) Foreign Application Priority Data

Mar. 16, 2022  (GB) ...................... 2203621

(51) Int. Cl.
*A61F 13/02*    (2024.01)

(52) U.S. Cl.
CPC .................. *A61F 13/023* (2013.01)

(58) Field of Classification Search
CPC ........ A61F 13/00; A61F 13/02; A61F 13/023; A61F 13/00021; A61F 2013/00089; A61F 2013/00582
USPC ................... 602/41–43, 54, 57, 58
See application file for complete search history.

(56) References Cited

U.S. PATENT DOCUMENTS

| | | | |
|---|---|---|---|
| 5,704,905 A * | 1/1998 | Jensen | A61F 13/0213 602/42 |
| 8,404,921 B2 | 3/2013 | Lee | |
| 2010/0125234 A1 | 5/2010 | Smith | |
| 2019/0008696 A1 | 1/2019 | Allen | |
| 2019/0125590 A1 * | 5/2019 | Rehbein | A61F 13/145 |
| 2019/0231604 A1 | 8/2019 | Holm | |

FOREIGN PATENT DOCUMENTS

WO    2020104426 A1    5/2020

OTHER PUBLICATIONS

International Preliminary Report on Patentability for International App. No. PCT/GB2023/050603; Dated Sep. 10, 2024; 6 pages.

* cited by examiner

*Primary Examiner* — Caitlin A Carreiro
(74) *Attorney, Agent, or Firm* — TAFT STETTINIUS HOLLISTER LLP; Ryan O. White; Derek B. Lavender (57) ABSTRACT

A wound dressing (10) includes a backing layer and a wound-site adhesive layer for adhering the backing layer to the wound. The backing layer has a shape including three lobes 14, 16, 18 in which each lobe is defined as an area enclosed by a pair of curved peripheral edges 14', 14", 16', 16", 18', 18" which meet at an apex located therebetween 14''', 16''', 18'''. Each lobe is separated from an adjacent lobe by a radial minima 26, 28, 30. The three lobes include a major lobe 14 and two minor lobes 16, 18. The major lobe has a length which is greater than each of the two minor lobes.

15 Claims, 3 Drawing Sheets

WOUND DRESSING

CROSS-REFERENCE TO RELATED DISCLOSURES

The present disclosure is a continuation of International Patent Application No. PCT/GB2023/050603 filed Mar. 15, 2023, which claims the benefit of GB Application No. 2203621.4 filed Mar. 16, 2022, the disclosure of which are incorporated herein by reference in entirety.

TECHNICAL FIELD OF THE INVENTION

The present invention relates to the shape of a wound dressing.

BACKGROUND TO THE INVENTION

It is known to make wound dressings for use on wounds to aid healing and prevent infections. Such dressings may be required to adhere to a patient's body in whichever location the wound is present. This may require a dressing to be adhered to areas which are variably or highly contoured or which experience a relatively high level of movement. This can make the initial adherence of the dressing challenging and limit subsequent wear time.

To address this problem, practitioners will often use additional securing means to attach a dressing which results in an additional time, cost, and reduced comfort for the patient. To help reduce this, manufacturers efforts have often focused on providing dressings with site specific shapes. However, this not lonely complicates design and manufacturing of the different shape types and sizes of the dressings, but also requires health care providers to stock many different types and sizes of dressings. Further, it requires practitioners to be educated and/or experienced in many different types of wound dressing to reduce the risk of the dressings being used incorrectly.

The present invention seeks to provide a multi-site wound dressing having a shape which helps alleviate some of the issues of existing dressing shapes.

SUMMARY OF THE INVENTION

The present invention provides a wound dressing according to the appended claims.

The present disclosure provides a wound dressing comprising: a backing layer; a wound-site adhesive layer for adhering the backing layer to the wound. The backing layer may have a shape comprising three lobes in which each lobe is defined as an area enclosed by a pair of curved peripheral edges which meet at an apex located therebetween with each lobe being separated from an adjacent lobe by a radial minima. The three lobes may comprise a major lobe and two minor lobes. The major lobe may be longer than each of the two minor lobes.

Advantageously, the pair of curved peripheral edges meeting at an apex, that is an abrupt discontinuity in the peripheral edges, provides for a preferential point about which the dressing can be folder or shaped. For example, a lateral curvature of the dressing away from a ridge on the body.

The length of the lobes may be measured as the perpendicular distance between the respective apex and a line which extends between the corresponding minima of each lobe.

The shape may have a single line of symmetry. The line of symmetry may extend between the radial minima which lies between the minor lobes and the apex of the major lobe. The line of symmetry may be a centre line.

The curved peripheral edges of each lobe may comprise a single radius of curvature.

A radius of curvature of the peripheral edges of the major lobe may be greater than the radius of curvature of the peripheral lobes of the minor lobes.

Each of the curved peripheral edges of each respective minor lobe may comprise different circumferential lengths such that the apex is off-centre with respect to the radial minima of each minor lobe.

The wound dressing may further comprise a wound contact layer for contacting a wound bed. The wound contact layer may have a shape comprising a major lobe and two minor lobes which correspond to the major and minor lobes of the backing layer. The peripheral edge of the wound contact layer may be located radially inwards of the peripheral edge of the backing layer.

The major and minor lobes of the wound contact layer may correspond to the backing layer in that there the lobes of the wound contact layer are located within the boundary of the respective lobes of the backing layer. In some embodiments, the radial minima of the wound contact layer and backing layer are generally aligned along a line which extends towards the central region of the dressing. In some embodiments, the wound contact layer and backing layer may correspond in shape in that at least one of the major or minor lobes of the wound contact layer is separated from the periphery edge of the backing layer by a uniform border.

In some embodiments, the radial separation between wound contact layer and the backing layer vary circumferentially. The varying radial separation may be limited to one or more of the lobes or regions of a lobe.

The radial separation between the wound contact layer and the backing layer may be greatest at the apex of a lobes. The increased radial separation may be provided at on the minor lobes. The increased separation may provide an increased adhesive border in a particular region, thereby allowing improved adhesion in an area of the dressing. Providing this at the minor lobes may be particularly advantageous.

The major lobe of the wound contact layer may comprise a pair of curved peripheral edges which meet at an apex. The minor lobes comprise a single continuously curving peripheral edge. Providing a continuous curvature on the minor lobes may allow the shape of the backing layer lobes to be a preferred shape whilst also providing an increased adhesive border area.

The single continuously curved peripheral edges of the minor lobes of the wound contact layer may comprise a single radius of curvature.

The wound dressing may further comprise a wound site adhesive layer on the backing layer. The radially outer edge of the adhesive layer may be coterminous with the radially outer edge of the backing layer. The radially inner edge of the adhesive layer may corresponds to the radially outer peripheral edge of the wound contact layer.

The adhesive layer and wound contact layer may radially overlap such that the adhesive layer is adhered to the wound contact layer.

The radial overlap between the wound contact layer and adhesive layer may be uniform around full circumference of the overlap.

A radius of curvature of the curved peripheral edges of the major lobe of the backing layer may have an origin which is contralateral with respect to the line of symmetry. The radii of curvature of the curved peripheral edges of the minor lobes may have origins which are ipsilateral with respect to the line of symmetry.

In a further aspect, the present disclosure provides a method of applying a dressing comprising: locating a dressing as disclosed or claimed herein over a wound site having a variously contoured surface; aligning an attachment axis of a major lobe of the dressing with an area of reduced contouring in the wound site and adhering it thereto, and, aligning attachment axes of the minor lobes with areas of increased contouring of the wound site and adhering them thereto.

It will be appreciated that the lesser and greater areas of contouring are relative to one another and the wound site to which they are applied in use.

In another aspect, the present disclosure may provide a method of applying a dressing comprising: locating a dressing as disclosed or claimed herein over a wound site having a variously contoured surface; aligning an attachment axis of a major lobe of the dressing with a ridge extending away from the wound, adhering the major lobe to the wound site such that an apex of the major lobe is proximate to the ridge and folding the curved peripheral edges of the major lobes down the flanks of the dressing, and, further adhering the minor lobes to the wound site.

It will be appreciated that, where possible, any feature or combination of features disclosed or claimed herein may be combined with any other feature or combination of features, whether or not this is explicitly described.

BRIEF DESCRIPTION OF THE DRAWINGS

In order that the invention may be more clearly understood one or more embodiments thereof will now be described, by way of example only, with reference to the accompanying drawings, of which.

DETAILED DESCRIPTION OF THE INVENTION

In the following detailed description, numerous specific details are set forth in order to provide a thorough understanding of various embodiments and the inventive concept. However, those skilled in the art will understand that the present invention: may be practiced without these specific details or with known equivalents of these specific details; is not limited to the described embodiments; and, may be practiced in a variety of alternative embodiments. It will also be appreciated that well known methods, procedures, components, and systems may have not been described in detail.

Generally, a wound dressing may be taken to be any dressing which is applied to a wound to promote healing and protect against further deterioration of the wound. Wound dressings will typically cover and be held in direct contact with a wound. A wound dressing will generally comprise a wound contacting surface and a rear surface which faces outwards from the wound and defines an exterior of the dressing.

The wound contacting surface may be provided by a separate wound contact layer which has specific properties to promote healing. Wound contact layers are typically non-adherent layers which are placed in direct contact with the wound and may be designed to promote the removal, e.g. by wicking or absorption, of exudate. The rear surface of the dressing may comprise a separate backing layer to provide the exterior of the dressing and aforementioned rear surface. The backing layer may be configured to provide a sealed envelope against the wound to prevent unwanted contamination of the wound, whilst being optionally breathable to allow moisture egress to aid dressing and wound healing performance. The backing layer may be any suitable material and may, in some embodiments, comprise a polyurethane material, as known in the art and may be LPT 9147 supplied by Covestro AG. The backing layer may have a thickness of between 25 microns and 35 microns, preferably 30 microns.

Wound dressings may be attached to a wound site by any known method of attachment, for example by binding with a bandage or use of adhesive tape, or with some other form of mechanical restraint which holds the dressing in place. In addition, or alternatively, the dressing may comprise a wound-site adhesive layer which is provided on the backing layer or portions of a wound contact layer so as to adhere the dressing to a wound site, as required.

In addition to the wound contact layer, it will be appreciated that many other types of layers may be included in a dressing. A dressing may comprise, for example, a backing layer for covering a wound and may further comprise one or more from the group comprising: a wound contact layer, a fluid distribution layer, a wicking layer, an absorbency layer, a superabsorbency layer, a transmission layer, a foam layer, a gauze layer, a wound-site adhesive layer or intralayer adhesive layer, amongst others. Where a wound dressing comprises a backing layer and one or more other layers, the additional layers will typically be provided in a stacked configuration in which the backing layer is provided as an outer layer which defines an external surface of the dressing which is typically adhered to the patient cover the wound and provide an envelope in which the other layers can be housed. Each of the layers may be described in relation to the backing layer and the wound site. Thus, each layer which is located between wound site and backing layer may comprise a first surface which faces inwardly and towards the wound site, and a second surface which faces outwardly from the wound site and towards the backing layer.

The wound dressing shape described herein may be used in any type of wound dressing. The specific embodiments described below comprise a backing layer, a wound contact layer and an adhesive layer, but this is not a limitation and one or more of these layers may not be present in some examples. For example, a wound dressing according to the present disclosure may comprise a backing layer only. Such a backing layer may be used to cover a separate wound contacting dressing for example. In other examples, the wound dressing may not comprise an adhesive layer but be attached to a patient using a secondary means, such as the aforementioned bindings or the like.

The wound dressings of the present disclosure are shaped to lend themselves to multiple different types of wound sites whilst have a broadly similar shape. In doing so, the wound dressings have increased utility and require less specialist knowledge to be applied. In providing a multi-site dressing shape, it is the intention to provide a dressing which balances ease of use with increased performance in terms of wear-time and patient comfort in numerous different circumstances.

Figure 1:
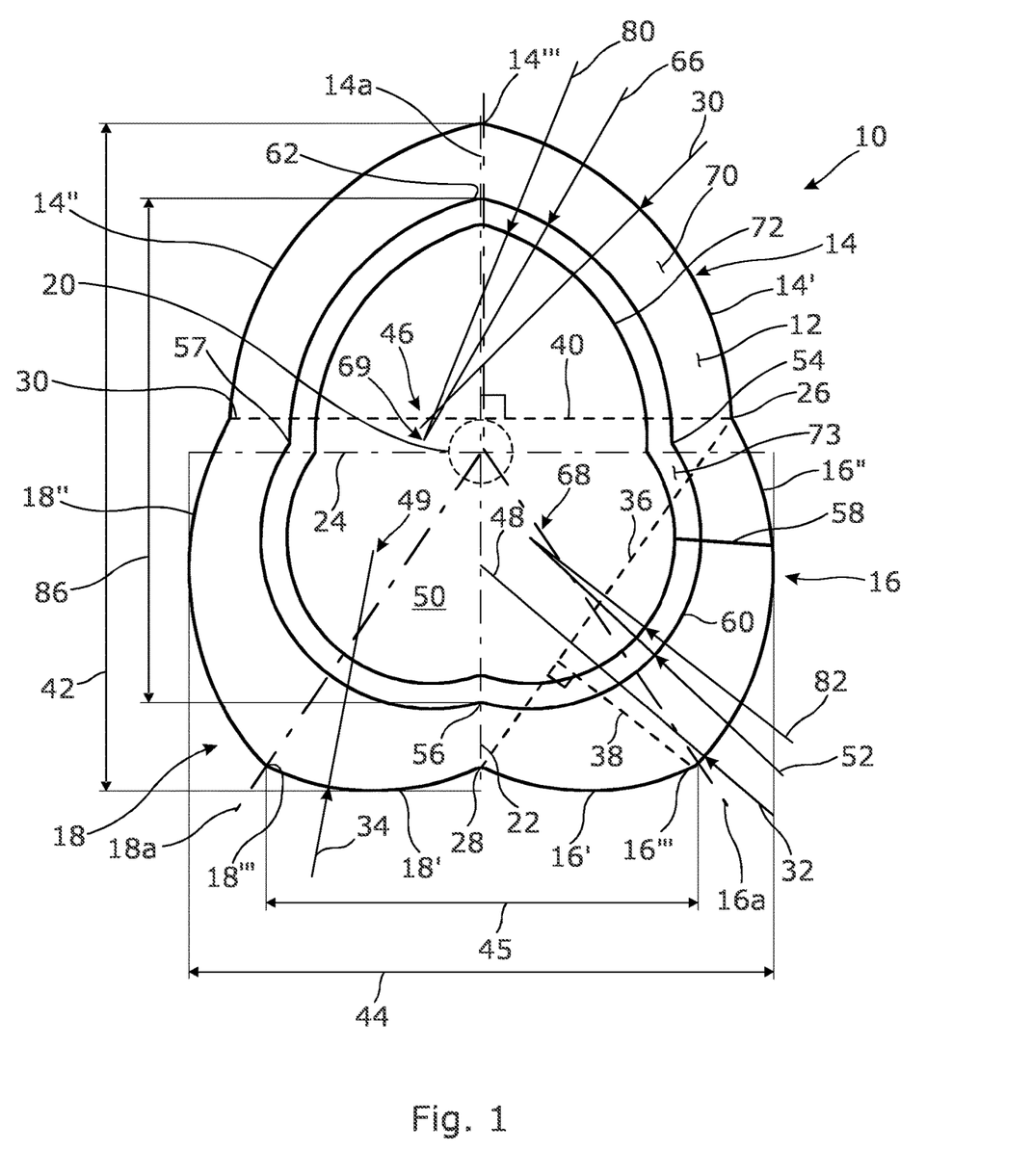
FIG. 1 shows a plan view of a dressing according to the present disclosure.
Figure 2:
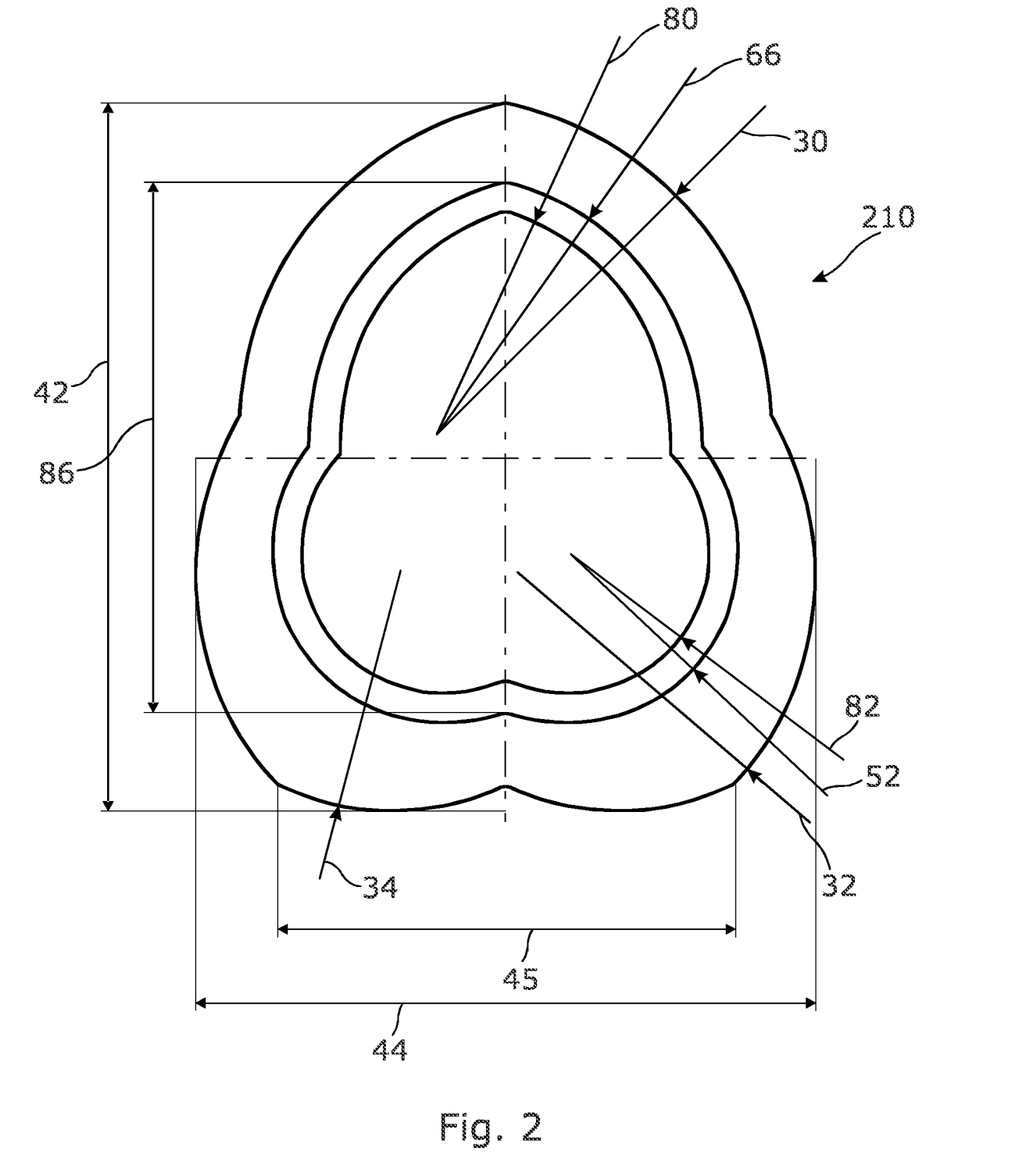
FIG. 2 shows a plan view of another dressing according to the present disclosure.
Figure 3:
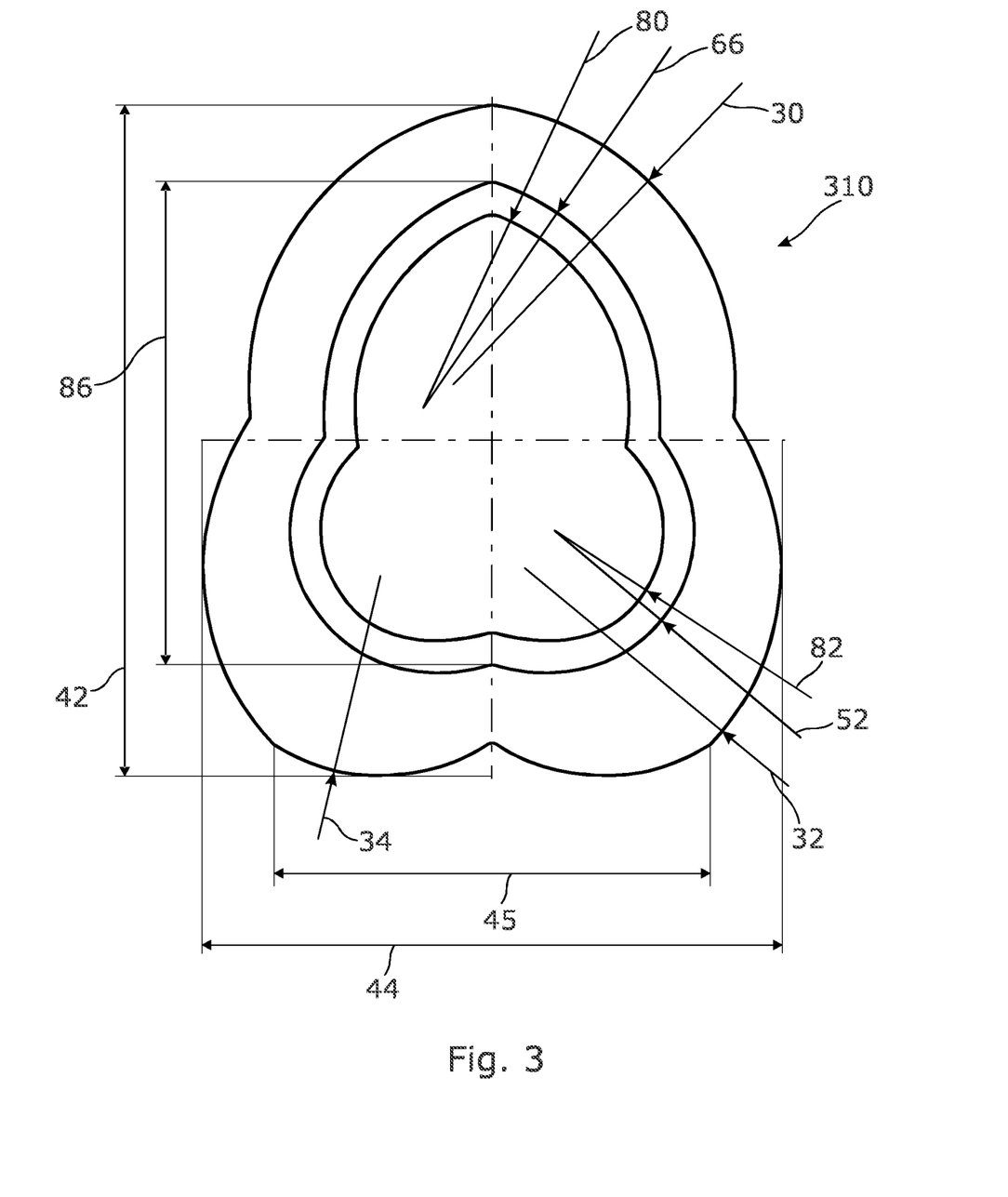
FIG. 3 shows a plan view of a further dressing according to the present disclosure.

FIGS. 1 to 3 show various dressing shapes according to the present disclosure. The dressings are considered to be favourable for attaching or adhering to multiple different sites on the human body. The differences between the dressings provided in FIGS. 1 to 3 principally relate to the relative size with the dressing 10 in FIG. 1 being a relatively large dressing, the dressing 210 of FIG. 2 being a mid-sized dressing, and the dressing 310 of FIG. 3 being a relatively small dressing. It will be appreciated that the terms "large", "mid-sized" and "small" are relative terms and used within the confines of this disclosure to differentiate the dressings 10, 210, 310 but there is no restriction on the absolute size and each of the dressings may be used without reference to the other dressings. Various proportions and sizes of specific embodiments are provided below in connection with the FIGS. 1 to 3, but these are not limitations.

The principal features which are common to each of the shapes are described primarily in connection with FIG. 1 below, but it will be appreciated that the features of the dressing shown in FIG. 1 may be applicable to all of FIGS. 1 to 3, unless specifically stated otherwise.

FIG. 1 shows a wound dressing 10 in plan. The dressing 10 comprises a backing layer 12 having a shape comprising three lobes 14, 16, 18 which extend radially outwards from a central region of the dressing. To aid the description of the dressing shape, there is shown a centre line 22 which extends centrally along the longitudinal axis of the dressing 10 and a transverse midline 24 which traverses the width of the dressing at the midpoint of the centre line 22. The dressing 10 may also include a plurality of notional lobe axes 14a, 16a and 18a, one for each lobe, which extend from the central region 20 through an apex of each lobe 14, 16, 18. The lobe axes 14a, 16a, 18a may be referred to as attachment axes, as expanded upon below. The central region of the dressing 10 may generally refer to the area in which a wound would be located when in use, i.e. within a border region of the backing layer or boundary of a wound contact layer for example. In some embodiments and for the purpose of the description, it may be useful to define the central region as a geometric centre 20 of the dressing 10 as provided by the intersection at the centre line 22 and transverse midline 24, as shown.

The three lobes 14, 16, 18 are angularly displaced from one another about the central region 20 and have sizes and shapes which are generally configured to allow the dressing 10 to conform more readily to different areas of a patient's body which are typically but not necessarily contoured and/or difficult areas to adhere a dressing to. These areas may include a shoulder, armpit, elbow, wrist, sacral region, breast, hip, and heel, for example.

Each of the lobes 14, 16, 18 may be defined as an area enclosed by a pair of curved peripheral edges 14', 14", 16', 16", 18', 18" which meet at an apex 14''', 16''', 18''' located therebetween. Hence, taking the first lobe 14 as an example, there is provided first 14' and second 14" curved peripheral edges which meet at a single apex 14''' and which enclose an internal area of the dressing 10. Adjacent lobes 14, 16, 18 may be meet at radial minima 26, 28, 30 located between the adjacent curved peripheral edges of adjacent lobes. The radial minima 26, 28, 30 shown in the drawings are defined by the change of direction of the peripheral edge at the intersection between adjacent curved areas. Thus, the radial minima 26, 28, 30 may comprise an abrupt transition or corner region rather than a sweeping curve between adjacent lobes. For example, the radius of curvature at the radial minima 26, 28, 30 may be less than 5 mm, optionally less than 3 mm, optionally less than 1 mm.

The curved nature of the peripheral edges 14', 14", 16', 16", 18', 18" and the local radial minima 26, 28, 30 which distinguish the lobes lend themselves to allowing the dressing 10 to fold and adapt to contoured regions more readily than other conventional dressings. The three lobes 14, 16, 18 which extend radially away from the central region 20 of the dressing may provide principal attachment axes, which can be taken to be the lobe axes 14a, 16a, 18a, which can curve to suit a broad range of wound site locations having varying contours. The radial minima 26, 28, 30 provide a natural fold line between the lobes allowing the three lobes 14, 16, 18 to be more readily conformed to the area surrounding a wound site in different directions whilst the curved peripheral edges 14', 14", 16', 16", 18' and 18" which extend between the apex 14''', 16''', 18'''' and the radial minima 26, 28, 30 help maximise the enclosed wound contact area. The combination of these features may provide for a preferable contouring of the dressing 10, increased adhesion and increased wear time.

It is of note that the majority of wound sites are surrounded by varying degrees of contouring and providing lobes with geometries which are better suited to a combination of large and small degrees of contouring in a single dressing is useful for ensuring increased attachment and conformability in the general case. The dressings of the present disclosure may comprise lobes 14, 16, 18 with a combination of major and minor lobes which are generally configured to be conformed to different radii of curvature. Thus, a major lobe may be longer or more elongate than a minor lobe and better suited to a larger radius of curvature, whereas, conversely, a shorter minor lobe may be better suited to a tighter radius of curvature. Further, it is also the case that the dressing 10 may be elongate such that the length of the centreline 22 is greater than the maximum width. This elongation can further aid the options for positioning the dressing to suit the contouring around a wound. It will be appreciated that providing this asymmetry in the size of the lobes 14, 16 and 18 allows the dressing 10 to suit irregularly contoured regions of the body without impacting the ability to adhere to contoured regions.

The apexes 14''', 16''' and 18''' which exist between and define the respective curved peripheral edges 14', 14", 16', 16", 18', 18" of each of lobes 14, 16, 18 provide for a preferential lateral curvature of the dressing away from the attachment axis 14a, 16a, 18a where required. Thus, where the dressing 10 is required on an area with a ridge, for example the elbow, the major attachment axis 14a can be aligned with the ulna with the flanks of the major lobe extending laterally around the forearm, and the minor lobes 16, 18 can be used to extend up and around the more gentle curves of the upper arm. The same principle applies to the apexes 16a, 18a of the minor lobes 16, 18 which may be advantageously extend laterally around the flanks of a contoured region of the wound.

The lobes 14, 16, 18 are circumferentially distributed around central region of the dressing 10 and wound site in use. In the image shown in FIG. 1, the principal axis of the dressing, i.e. centreline 22, extends from the apex 14a of the major lobe 14 to the radial minima 28 between the minor lobes 16, 18. The separation of the apexes 16''', 18''' of the minor lobes 16, 18 from the centre line 22 may be equal on each side thereby providing the dressing 10 with a single line of symmetry. However, it will be appreciated that the separation may be non-uniform in some applications and there may not be a single line of symmetry. The line of symmetry may be useful for simplifying the shape of the dressing to make the orientation and placement more straightforward for a practitioner in use.

As noted, the major lobe 14 may be greater in length than the minor lobes, 16 and 18 and/or may be elongate. The length of the lobes 14, 16, 18 may be measured as the perpendicular distance between the respective apex 14''', 16''', 18''', and a line which extends between the corresponding minima 26, 28, 30 of each lobe. Hence, as shown in FIG. 1, there is a line 36 which extends between the minima 26, 28 of the right hand side minor lobe 16, and line 38 which extends perpendicularly therefrom towards the apex 16'''. Similarly, line 40 extends between the minima 26, 30 of major lobe 14 so as to be perpendicular to the centre line 22, with the length of the centre line 22 which extends between line 40 and apex 14''' defining the length of the lobe 14. As such, it can clearly be seen that the length of line 38 is around half that of the length of the portion of centre line 22 which extends line 40 and the apex 14'''. Although not shown, lines 36 and 38 can be replicated for minor lobe 18.

The width of a lobe may be defined as by the separation between the radial minima. The width of the major lobe 14, as defined by line 40, may be greater than the width of the minor lobes 16, 18, as defined by line 36. Further, the aspect ratio, that is, the length to width ratio, may be greater for the major lobe 14 when compared to the minor lobes 16, 18.

The angular the separation between each of the lobes 14, 16, 18 about the central region 20 may be the same in some applications. Hence, an attachment axis 14a, 16a, 18a which extends through each of the lobe apexes 14''', 16''', 18''' to a central region 20 may be equal, e.g. 120 degrees. However, as can be seen in FIG. 1, in some preferred arrangements the angle between the minor lobes 16, 18 may be less than the angle between each respective minor lobe 16, 18 and the major lobe 18. In some embodiments the angular separation between the minor lobes 16, 18 may be between 45 degrees and 120 degrees, or between 60 degrees and 90 degrees. The separation between the major lobe 14 and the minor lobes 16, 18 may be between 120 degrees and 157.5 degrees. The distance 45 between the apexes 16''', 18''' of the minor lobes 16, 18 may be between 250 mm and 120 mm. In a large dressing 10, as shown in FIG. 1, the separation may be between 250 mm and 140 mm, optionally between 200 mm and 150 mm, optionally between 180 mm and 160 mm. In a medium sized dressing, as shown in FIG. 2, the distance may be between 225 mm and 130 mm, optionally between 160 mm and 140 mm. In a small dressing, as shown in FIG. 3, the separation may be between 210 mm and 120 mm, optionally, between 150 mm and 130 mm.

The curved peripheral edge of the dressing 10 may be defined by multiple radii to provide a change in the curvature along each edge portion. However, in the example shown in FIG. 1, the curvature of each of the peripheral edges 14', 14", 16', 16", 18', 18" of the lobes 14, 16, 18 are shown as each having a single radius of curvature. More specifically, both the peripheral edges 14', 14" of the major lobe 14 comprise a first radius 30 of curvature and the minor lobes comprise a first 32 and a second 34 radius of curvature, one for each of the edges 16', 16" and 18', 18". It will be appreciated that the first 32 and second 34 radii of the minor lobes 16 and 18 are the same for each of the lobes 16, 18 due to symmetry of the dressing 10. However, this need not be the case and the minor lobes 16 and 18 may not correspond in this way.

Generally, the radius of curvature 30 for the peripheral edges 14', 14" of the major lobe 14 may be greater than the radii of curvature 32, 34 of the peripheral edges of the minor lobes 16, 18 to provide the elongate form. In the embodiment shown, the radius 32 of the lateral peripheral edges 16", 18" of the minor lobes 16, 18 is greater than the adjacent peripheral edge 16', 18' which is adjacent to and extends from the central axis 22 of the dressing 10.

The radii 30 of the major lobe 14 may vary between 150 mm and 70 mm. For a large dressing, as shown in FIG. 1, the radius 30 may be between 150 mm and 100 mm, preferably between 130 mm and 110 mm. For a medium sized dressing, as shown in FIG. 2, the radius 30 may be between 130 mm and 90 mm, preferably between 120 mm and 100 mm. For a small dressing, as shown in FIG. 3, the radius 30 may be between 110 mm and 70 mm preferably between 100 mm and 80 mm.

The circumferential length of the lateral and adjacent peripheral edges 16', 16". 18', 18" of the minor lobes 16, 18, may be different from each other such that the apex 16''', 18''' is off-centre with regards to the two radial minima (26, 28 and 28, 30) which define each of the minor lobes 16, 18. The longer edge may form the lateral edge 16", 18" of the dressing, that is the edge which is laterally distal with respect to the centre line 22, with the shorter edge 16', 18' being adjacent to and extending from the centre line 22. As such, the apex 16''', 18''' of the minor lobes 16, 18 is presented closer to the centre line 22 of the dressing 10 and more distal in relation to the transverse midline 24. Hence, increasing the relative length of the adjacent edge will move the apex laterally away from the centre line 22, and increasing the relative length of the lateral edge will move the apex away from the transverse midline 24.

The radius 32 of the lateral peripheral edge 16", 18" may vary between 135 mm and 60 mm. For a large dressing, as shown in FIG. 1, the lateral radius 32 may be between 135 mm and 95 mm, preferably between 125 mm and 105 mm. For a medium sized dressing, as shown in FIG. 2, the lateral radius 32 may be between 120 mm and 80 mm, preferably between 110 mm and 90 mm. For a small dressing, as shown in FIG. 3, the lateral radius 32 may be between 105 mm and 60 mm preferably between 95 mm and 75 mm.

The radius 34 of the adjacent peripheral edge may vary between 115 mm and 45 mm. For a large dressing, as shown in FIG. 1, the adjacent radius 34 may be between 115 mm and 75 mm, preferably between 105 mm and 85 mm. For a medium sized dressing, as shown in FIG. 2, the adjacent radius 34 may be between 100 mm and 60 mm, preferably between 90 mm and 70 mm. For a small dressing, as shown in FIG. 3, the adjacent radius 34 may be between 85 mm and 45 mm preferably between 75 mm and 55 mm.

The size of the dressings 10, 210, 310 may be denoted by length 42 and width 44. The length 42 may be taken to be along the central axis 22 and defined by the most extreme points of the peripheral edge. The length may be between 300 mm and 180 mm. The width 44 may be taken to be the greatest lateral dimension of the dressing 10, 210, 310 with respect to the longitudinal axis which may be between 260 mm and 150 mm. With regards to the different sizes shown in FIGS. 1 to 3, the large dressing may comprise a length 42 of between 300 mm and 220 mm, preferably between 275 mm and 245 mm. The medium sized dressing may have a length 42 between 255 mm and 215 mm, preferably between 245 mm and 225 mm. The small dressing may have a length 42 between 240 mm and 200 mm, preferably between 230 mm and 210 mm.

With regards to the different sizes shown in FIGS. 1 to 3, the large dressing may comprise a width 44 of between 250 mm and 210 mm, preferably between 240 mm and 220 mm. The medium sized dressing may have a width 44 between 225 mm and 185 mm, preferably between 215 mm and 195 mm. The small dressing may have a width 44 between 215 mm and 155 mm, preferably between 200 mm and 180 mm.

It will be appreciated that the above sizes are provided as examples only and other sizes will be possible within the scope of the present disclosure.

The origins of the various radii for the peripheral edges of the major lobes and the lateral and adjacent edges of the minor lobes may be selected to determine the overall shape of the dressing. In the examples shown in FIGS. 1 to 3, the origins 46 of the radii 30 of the peripheral edges 14', 14", of the major lobe 14, are located in the upper contralateral quadrant of the dressing 10. Thus, as can be seen in FIG. 1, the radii 30 of the right hand curved peripheral edge 14" of the major lobe 14 has its origin 46 on the left-hand side of the centre line 22 and above the transverse midline 24, with the left hand edge having its origin on the right hand side (not shown).

The origins 48, 49 of the radii 32 and 34 which define the lateral 16", 18" and adjacent 16''', 18''' edges may be located in the lower ipsilateral quadrant for each respective edge. It will be appreciated that the locations of the origins 48 and 49 will typically be different to one another to allow the off-centre apexes, where present. Further, it will also be appreciated that the locations of all of the origins 46, 48 and 49 may vary to suit different sizes of dressings 10 and to provide different aspect ratios.

As noted above, the dressing 10 may comprise a wound contact layer 50 which is provided to contact the wound in use. The wound contact layer 50 is provided across a central region of the dressing 10 typically provided radially inwards of the peripheral edge of the backing layer 12, to provide a border region therebetween. The border region may comprise an adhesive layer which is described in more detail below.

As noted above, wound contact layers are generally well known in the art and any suitable wound contact layer may be used. An example of a suitable wound contact layer may be that described in EP2498829 which discloses a wound dressing having an absorbent component for a wound contact layer. The wound contact layer may comprise gel forming fibres which are bound to a foam layer to aid the absorption of wound exudate; however, this is not a limitation, and any type of wound contact layer may be used.

The shape of the wound contact layer 50 may generally correspond to the backing layer 12 and may comprise a major lobe and two minor lobes which are clearly seen in the figures and not provided with separate reference numerals for the sake of clarity. The lobes of the wound contact layer 50 may largely correspond to those of the backing layer 12 so much of the description is not repeated for the sake of brevity. Features relating to some points of differentiation between the wound contact layer 50 and backing layer 12 are now presented.

In contrast to the backing layers 12 shown in FIGS. 1 to 3, the minor lobes of the wound contact layer 50 may not have an apex but instead comprise peripheral edge 60 comprising a continuous curve. The continuous curvature of the wound contact layer minor lobes may comprise a single radius 52 and may extend between the radial minima 54, 56 which define and demarcate the lobes. However, it will be appreciated that the minor lobes of the wound contact layer 50 may correspond more closely to the backing layer 12 so as to include an apex such that the border region between the backing layer peripheral edges 16', 16" and the wound contact layer peripheral edge 60 is uniform.

By providing different peripheral edge profiles for the wound contact layer 50 and the backing layer 12, it can be seen that the radial width 58 of the border region between the backing layer 12 and wound contact layer 50 may be varied. More particularly, by providing an apex 16''', 18''' in the backing layer 12 profile and a constant curvature in the wound contact layer 12 profile, it allows the radial width 58 of the border to be increased in predefined areas. In FIG. 1, the radial width 58 is greatest in the region of the apex 16''', 18''' for each lobe, with a maximum lying along the attachment axis 16a, 18a. In other words, the radial separation between wound contact layer 50 and the backing layer 12, e.g. the radial width, may vary circumferentially, e.g. around the periphery of the backing layer 12 and the radial separation between the wound contact layer 50 and the backing layer 12 may be greatest at the apex 16''', 18''' of the minor lobes 16, 18 of the backing layer 12.

In embodiments which include an adhesive layer in the border region between the backing layer 12 and wound contact layer 50, the increased area around the apex region of the minor lobes 16, 18 can provide a greater area of adhesion so as to improve the retention of the dressing 10, particularly around areas which are generally more contoured. Further, providing an apex 16, 18 on the backing layer 12 and a more rounded wound contact layer 50 allows the conformability of the dressing 10 to be increased whilst having a minimal impact on the wound contacting performance of the dressing 10 as the backing layer is generally more conformable.

It will be appreciated, that although the major lobe 14 is shown as comprising a correspondingly shaped wound contact layer 50 with an apex 62 to provide a uniform border region, this is optional and the apex 62 could be omitted in some embodiments and a continuous curvature provided. It will also be appreciated that each of the lobes of the wound contact layer 50 may be provided with an apex whilst also providing a non-uniform border region. This may be achieved, for example, off-setting the origins of the edge radii for the backing 12 and wound contact layers 50.

The radial minima 54, 56, 57 which define the lobes of the wound contact layer 50 are generally radially aligned with those of the backing layer 12 such that the angular separation between the radial minima 54, 56, 57 is the same each of the backing layer 12 and wound contact layer 50. Hence, the radial width 58 of the border region may be equal on either side of the minima. In the examples shown, the radial minima 28, 56 between the minor lobes of the backing layer and the wound contact layer are both shown as being on the centre line 22 of the dressing 10. The radial minima 26, 54 between the major lobes and minor lobes of the backing layer and wound contact layer 50 are joined by a radial line which extends towards the centre line with an intersection with the centre line 22 being provided below the mid-point of the centre line 22. It will be appreciated that the radial line which extends through the minima may be used to define a geometrical centre of the dressing at the intersection with the centre line 22. This may be useful for defining some aspects of the dressing 10 in some instances.

As with the backing layer 12, the curved peripheral edge 60 of the wound contact layer 50 may be defined by multiple radii to provide a graduation or other change in the curvature. However, in the example shown in FIG. 1, the curvature of each of the peripheral edges of all of the wound contact layer lobes are shown as each having a single radius of curvature 52, 66. More specifically, both the peripheral edges of the major lobe comprise a first radius of curvature 66 and the minor lobes comprise a second, single radius of curvature 52.

Generally, the radius 66 of curvature for the peripheral edges of the wound contact layer major lobe is greater than the radius of curvature of the peripheral lobes of the minor lobes.

The radius 66 of the wound contact layer major lobe edges may vary between 120 mm and 55 mm. For a large dressing, as shown in FIG. 1, the radius may be between 120 mm and 80 mm, preferably between 110 mm and 90 mm. For a medium sized dressing, as shown in FIG. 2, the radii may be between 110 mm and 70 mm, preferably between 100 mm and 80 mm. For a small dressing, as shown in FIG. 3, the radius may be between 100 mm and 60 mm preferably between 90 mm and 70 mm.

The radius of the wound contact layer minor lobe peripheral edge may vary between 85 mm and 25 mm. For a large dressing, as shown in FIG. 1, the radius may be between 85 mm and 45 mm, preferably between 75 mm and 55 mm. For a medium sized dressing, as shown in FIG. 2, the radius may be between 75 mm and 35 mm, preferably between 65 mm and 45 mm. For a small dressing, as shown in FIG. 3, the minor lobe radius may be between 65 mm and 25 mm preferably between 55 mm and 35 mm.

The origins 68, 69 of the various radii for the peripheral edges of the wound contact layer 50 may be within the same quadrant as the backing layer radii origins 46, 48. Hence, the major lobe origin 69 may be in the contralateral upper quadrant with respect to the centre line 22 and may be generally concentric with the backing layer origins 46 in some embodiments. The minor lobe origin 68 may be in the lower ipsilateral quadrant. As will be appreciated given the relative geometries of the backing layer 12 and the wound contact layer 50, the origins for each will be separate from one another.

The size of the wound contact layer 50 may be denoted by length 86 and a width (not marked). The length 86 may be taken to be along the central axis 22 and defined by the most extreme points of the peripheral edge and the width may be provided by the maximum transverse dimension of the wound contact layer (similar to the width of the backing layer). The length and width may be between 0 mm and 40 mm less than the length and width of the backing layer for each respective dressing.

As noted above, the dressing described herein may be attached to a wound site using a suitable attachment system such as a binding, such as a bandage, adhesive tape, or some other form of mechanical restraint which holds the dressing in place. In addition, or alternatively, the dressing 10 may comprise a wound-site adhesive layer 70 which is provided on the backing layer 12 so as to adhere the dressing to a wound site, as required.

The wound-site adhesive layer 70 may be provided only in a peripheral or border region of the dressing such that a central region does not include the wound-site adhesive layer 70. Hence, the adhesive layer 70 may comprise a window through which the wound contact layer 50 is exposed for direct contact with the wound when in use. The window may extend over a central region of the dressing 10 and may be defined by an internal edge 72 of the adhesive layer 70. The internal edge 72 may correspond to the shape of the wound contact layer 50 and/or the shape of the backing layer 12. Hence, the internal edge 72 of the adhesive layer 70 may comprise a lobed profile such that the window through which the wound contact layer 50 is exposed comprises a lobed pattern of a similar form to the wound contact layer outer peripheral edge, and/or the edge of the backing layer 12.

In the examples shown in FIGS. 1 to 3, the adhesive layer 70 has an outer peripheral edge which is coterminous with the outer peripheral edge of the backing layer 12 allowing a full peripheral adhesion of the dressing 10 around the wound site.

As shown. the adhesive layer 70 may overlap the wound contact layer 50 at the inner edge 72 of the adhesive layer 70 such that the adhesive layer 70 is adhered to the wound contact layer 50. This may be advantageous to fix the wound contact layer 50 in place with respect to the backing layer 12. The radial overlap may be uniform around the periphery of the wound contact layer 50. The radial extent of the overlap may be between 0 mm and 20 mm. In some embodiments the radial overlap may be between 5 mm and 15 mm, optionally 10 mm. Given this it will be appreciated that the various radii sizes and origins described above for the wound contact layer 50 may be applicable to the adhesive layer 70. However, the sizes of the radius 80 for the major lobe of the adhesive layer 70, and radius 82 for the minor lobe may be between 0 mm to 20 mm less in each instance.

The wound-site adhesive layer 20 may be any suitable adhesive and may comprise a pressure sensitive adhesive as known in the art. The adhesive layer may be a hydrocolloid, polyurethane, rubber-based adhesive, acrylic adhesive or silicone adhesive. Acrylic adhesives are known to provide reasonable adhesion human skin but are generally not repositionable. Silicone adhesives also provide a good adhesion to human skin but are hydrophobic and so provide a barrier to exudate and limits MTVR. The silicone adhesive may be any suitable silicone adhesive such as Dow Corning 9900, Dow Corning 9800, Dow Corning 1020, P-Derm PS2180, P-Derm-PS-2189, P-Derm PS-2190, P-Derm PS-2192 or Wacker 2117, Wacker Silpuran 2114, Brightwake High Tack Silicone etc. The base weight of the adhesive layer may be in a range of between 70 gsm and 200 gsm. For example, the base weight may be 70 gsm, 80 gsm, 100 gsm, 130 gsm, 150 gsm, or 200 gsm.

The wound-site adhesive layer 70 may include perforations (not shown). The perforations may be provided to improve the performance of the dressing in terms of the rate of exudate absorption, adhesion duration, i.e. wear time, for the dressing, and versatility of the dressing that is, the range of exudate levels the dressing may be used for.

FIGS. 1 to 3 will now be described as specific, non-limiting, examples. As such, FIG. 1 may comprise a dressing 10 having a backing layer width of 228 mm and a length of 261 mm. The transverse separation of the minor lobe apexes (relative to the centre axis) may be 168 mm. The peripheral edge radius of the major lobe may be 122 mm, the lateral edge radius of the minor lobe may be 113 mm and the adjacent edge radius may be 95 mm. With regard to the wound contact layer, the major lobe radii may be 97 mm and the minor lobe radii may be 67 mm. The adhesive layer may have major lobe radii of 87 mm and minor lobe radii of 57 mm.

An exemplary medium dressing as shown in FIG. 2 may have a backing layer width (transverse to the centre axis) of 204 mm and a length of 235 mm. The transverse separation of the minor lobe apexes may be 150 mm. The peripheral edge radius of the major lobe may be 107 mm, the lateral edge radius of the minor lobe may be 99 mm and the adjacent edge radius may be 80 mm. With regard to the wound contact layer, the major lobe radii may be 87 mm and the minor lobe radii may be 57 mm. The adhesive layer may have major lobe radii of 77 mm and minor lobe radii of 47 mm.

An exemplary small dressing as shown in FIG. 3 may have a backing layer width (transverse to the centre axis) of 188 mm and a length of 218 mm. The transverse separation of the minor lobe apexes may be 142.5 mm. The peripheral edge radius of the major lobe may be 92 mm, the lateral edge radius of the minor lobe may be 84 mm and the adjacent edge radius may be 65 mm. With regard to the wound contact layer, the major lobe radii may be 77 mm and the minor lobe radii may be 46 mm. The adhesive layer may have major lobe radii of 67 mm and minor lobe radii of 36 mm.

The one or more embodiments are described above by way of example only. Many variations are possible without departing from the scope of protection afforded by the appended claims.

The invention claimed is:

1. A wound dressing comprising:
a backing layer; and
a wound-site adhesive layer for adhering the backing layer to a wound,
wherein the backing layer has a shape comprising three lobes in which each lobe is defined as an area enclosed by a pair of curved peripheral edges which meet at an apex located therebetween with each lobe being separated from an adjacent lobe by a radial minima, wherein the three lobes comprise a major lobe and two minor lobes, wherein the major lobe has a length which is greater than a length of each of the two minor lobes,
wherein each of the curved peripheral edges of the pair of curved peripheral edges of each respective minor lobe comprises different radii of curvature, and
wherein each of the curved peripheral edges of the pair of curved peripheral edges of each respective minor lobe comprises different circumferential lengths such that the apex is off-centre with respect to the radial minima of each minor lobe.

2. The wound dressing of claim 1, further comprising a wound contact layer for contacting a wound bed, wherein the wound contact layer has a shape comprising a major lobe and two minor lobes which correspond to the major and minor lobes of the backing layer, wherein the peripheral edge of the wound contact layer is located radially inwards of the peripheral edge of the backing layer.

3. The wound dressing of claim 2, further comprising a wound site adhesive layer on the backing layer, wherein a peripheral outer edge of the adhesive layer is coterminous with the peripheral edge of the backing layer, and an internal edge of the adhesive layer corresponds to the shape of the peripheral edge of the wound contact layer.

4. The wound dressing of claim 3, wherein the adhesive layer and wound contact layer radially overlap such that the adhesive layer is adhered to the wound contact layer.

5. The wound dressing of claim 4, wherein the radial overlap between the wound contact layer and adhesive layer is uniform around a full circumference of the overlap.

6. The wound dressing of claim 2, wherein a radial separation between wound contact layer and the backing layer varies circumferentially.

7. The wound dressing of claim 6, wherein the radial separation between the wound contact layer and the backing layer is greatest at the apex of the minor lobes.

8. The wound dressing of claim 1, wherein the shape has a single line of symmetry.

9. The wound dressing of claim 1, wherein a line of symmetry extends between the radial minima which lies between the minor lobes and the apex of the major lobe.

10. The wound dressing of claim 1, wherein a radius of curvature of the pair of curved peripheral edges of the major lobe is greater than the radii of curvature of the pairs of curved peripheral edges of the minor lobes.

11. The wound dressing of claim 1, wherein a line of symmetry extends between the radial minima which lies between the minor lobes and the apex of the major lobe, wherein a radius of curvature of each one of the curved peripheral edges of the major lobe of the backing layer has an origin which is contralateral with respect to the line of symmetry.

12. The wound dressing of claim 1, wherein a line of symmetry extends between the radial minima which lies between the minor lobes and the apex of the major lobe, wherein the radii of curvature of the pair of curved peripheral edges of each of the minor lobes have origins which are ipsilateral of the line of symmetry.

13. The wound dressing of claim 1, wherein the pair of peripheral edges of each of the minor lobes comprises a lateral peripheral edge and an adjacent peripheral edge adjacent to and extending from a central axis of the dressing, the radius of each lateral peripheral edge being greater than the radius of the adjacent peripheral edge.

14. The wound dressing of claim 1, wherein a length of each of the three lobes is measured as the perpendicular distance between the respective apex of each lobe and a line which extends between the corresponding radial minima of each lobe.

15. The wound dressing of claim 1, wherein a length to width aspect ratio is greater for the major lobe as compared to the two minor lobes.

* * * * *